United States Patent [19]

Davis

[11] 4,350,488
[45] Sep. 21, 1982

[54] DENTAL PULP TESTER

[76] Inventor: Laurance B. Davis, 3417 E. Turquoise, Phoenix, Ariz. 85028

[21] Appl. No.: 278,834

[22] Filed: Jun. 29, 1981

[51] Int. Cl.³ .............................................. A61C 3/00
[52] U.S. Cl. .................................................... 433/32
[58] Field of Search ...................... 433/32; 128/303.16

[56] References Cited

U.S. PATENT DOCUMENTS 3,274,995  9/1966  Eidus ...................................... 433/32
3,618,590  11/1971  Yardley ................................. 433/32

Primary Examiner—Robert Peshock
Attorney, Agent, or Firm—Drummond, Nelson & Nissle

[57] ABSTRACT

Apparatus for applying heat and cold to a tooth to determine if the nerves in the pulp of the tooth are alive. The apparatus includes a housing; a thermoelectric module carried in the housing including a plurality of semiconductor elements connected at their ends by a pair of opposed groups of electrically conductive plates to form an electrical series of the semiconductor elements, each of the pair of plate groups constituting hot junctions when electrical current passes through the series in one direction and constituting cold junctions when electrical current passes through the series in the reverse direction; a primary heat transfer member in thermally conductive contact with one of the pair of plate groups; a secondary heat transfer member in thermally conductive contact with the other of the pair of plate groups, the secondary heat transfer member including a thermally conductive casing, and passage means formed within the casing to receive and carry fluid therethrough and including at least one inlet and one outlet opening; conduits for directing fluid into the inlet opening of the passage means and for receiving fluid flowing through the outlet opening; terminals for making electrical contact with the thermoelectric module; a source of current electrically connected to the terminals; normally closed switch means connected between the terminals and the current source; and, a thermocouple unit in thermal contact with said primary heat transfer member for measuring the temperature of the primary heat transfer and for causing the switch means to open when the temperature of the primary heat transfer member reaches a preselected level.

3 Claims, 6 Drawing Figures

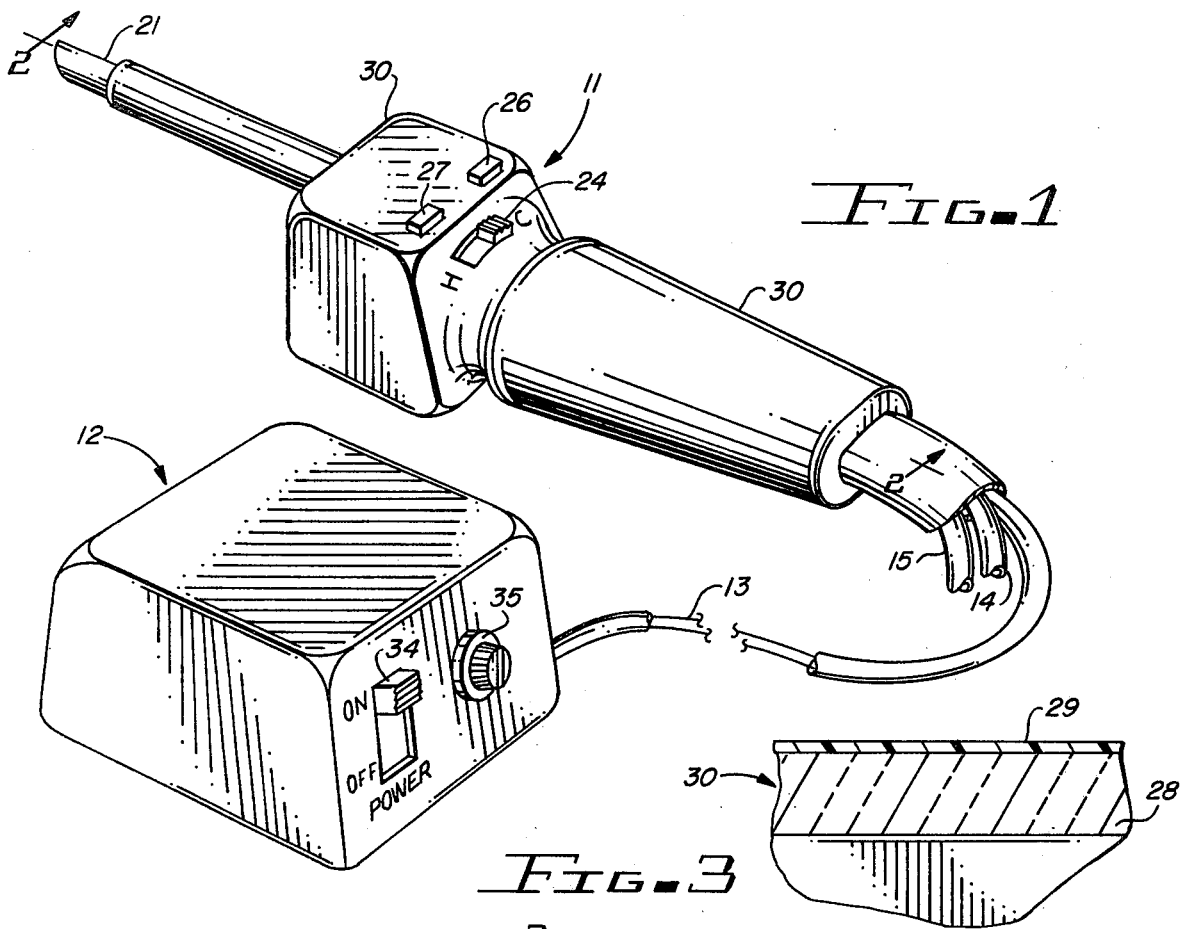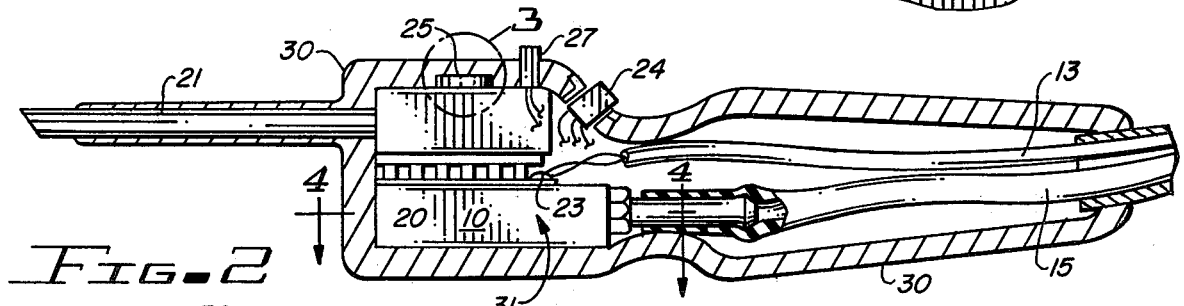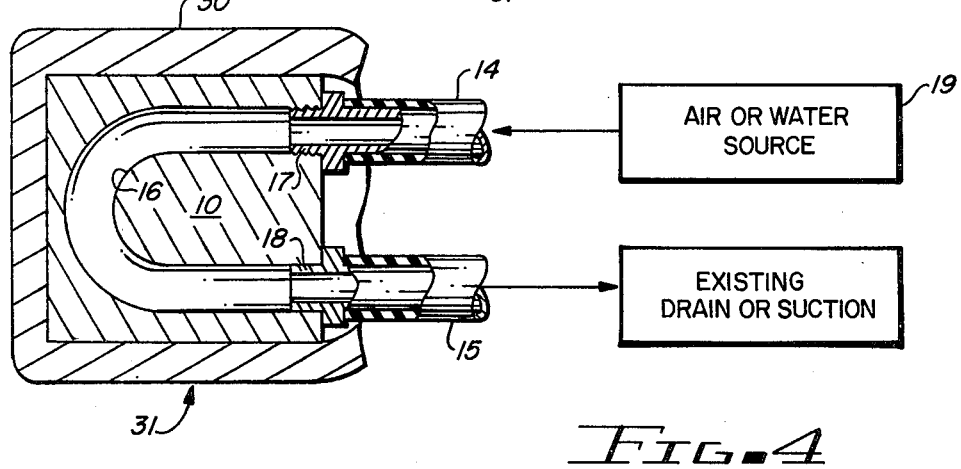

DENTAL PULP TESTER

This invention relates to dental apparatus.

More particularly, the invention concerns a dental pulp tester for applying heat and cold to a tooth to determine if the nerves in the pulp of the tooth are alive.

In a further and more specific respect the invention concerns a dental pulp tester which includes a thermally conductive probe which is contacted with a tooth to determine if the tooth is alive and includes a thermoelectric module for generating heat and cold which are, as desired, separately conducted through the probe to the tooth surface, the thermoelectric module comprising a group of semiconductor elements connected at their ends by a pair of opposed groups of electrically conductive plates to form an electrical series of the semiconductor elements, each of the pair of plate groups constituting hot junctions when electrical current passes through the series of semiconductors in one direction and constituting cold junctions when electrical current passes through the series of semiconductor elements in the reverse direction.

In another respect the invention relates to an improved dental pulp tester of the type described having an improved system for controlling the transfer of heat from the thermoelectric module to the probe which markedly reduces the amount of electricity consumed during operation of the probe and extends the operational life of the semiconductor elements comprising the thermoelectric module.

In order to determine whether the nerves in the pulp of a patient's tooth are alive and the tooth can be saved without having to perform a root canal, dentists customarily apply heat and cold to the tooth to see if the patient experiences pain during either application. Dentists apply both heat and cold because sometimes the nerves in the tooth pulp will respond only to cold or to heat. The standard procedure for applying heat or cold to a tooth is to contact the tooth with ice or the heated end of a wax stick. Since using the ice or wax stick is somewhat awkward and because the wax stick may not generate sufficient heat to accurately determine if the tooth is alive, various types of electric dental pulp testing devices have been developed to perform the function of the ice and of the heated wax stick. See for example U.S. Pat. Nos. 3,782,366 to Brown, 3,841,311 to Brown, 3,618,590 to Yardley et al and 3,274,995 to Eidus. Some of these dental pulp testing devices, for instance those disclosed in Eidus and Yardley, utilize thermoelectric modules to generate heat and cold which are separately conducted along a metal probe to the tooth. Such modules have been long known and are comprised of a series of semiconductor elements connected at their ends by a pair of opposed groups of electrically conductive plates to form an electrical series of the semiconductor elements. The plates in each group generally lie in a plane and become hot when electrical current passes through the series in one direction and cold when electricity passes through the semiconductors in the reverse direction. Consequently, if a metal probe is thermally connected to one group of conductive plates, the probe can be warmed or cooled depending on the direction in which current is permitted to flow through the semiconductors.

The principal problem associated with such semiconductors is that a substantially greater amount of heat than cold is generated per unit of electricity, and unless an efficient heat transfer system is used to draw away excess heat, heat generated by one group of plates will overcome cold generated by the opposing plane of plates. As a result, apparatus such as that shown in the Eidus and Yardley patents has been developed which incorporate heat sinks for drawing heat away from one group of plates when the opposing group of plates is being utilized to cool a metal probe.

The dental pulp tester described in Eidus includes an elongate metal handle having a thermoelectric module-probe pair attached at the left and right ends thereof with one of the two groups of electrical plates which connect the semiconductors in each module being in thermal contact with the metal handle. At the right hand end of the handle the plates forming the cold junctions contact the metal handle and the plates forming the hot junctions heat the attached probe (identified by reference character 20 in FIG. 1). At the left hand end of the handle the plates forming the hot junctions contact the metal handle and the plates comprising the cold junctions cool the other probe (identified by reference character 18 in FIG. 1). In use the mass of the metal handle is intended to function as a heat sink which draws heat and cold away from the right and left hand end thermoelectric modules, respectively. Since the thermoelectric modules generate much more heat per unit of electricity than cold, it is particularly important that excess heat be carried away from the module on the left hand end of the metal handle. However, as the portion of the handle near surface 40 accumulates heat it actually develops into a kind of reverse action heat source which supplies heat to the thermocouple module and drives up the temperature of the hot junctions and, consequently, the cold junctions thermally connected to probe 18. Over time, such heat accumulation markedly affects the degree to which the left hand thermoelectric module cools probe 18 and can cause the semiconductor elements of the module to fracture or otherwise be damaged. At the least, the heat accumulation in the metal handle substantially increases the electricity consumed during operation of the probe.

The fluid cooled heat sink depicted in the Yardley patent is a more efficient means for drawing heat away from the bottom side of the thermoelectric module (identified by reference character 13 in FIGS. 1–4) when cold is being generated on the upper surface of module 13 next to the metallic tip (reference character 14) of the pulp tester. Heat is most effectively dissipated by a fluid cooled heat sink when the heat absorbing wall of the sink is relatively thin and the flow of cooling fluid passes reasonably close to heat source. Thus in Yardley the fluid passages which are formed near the bottom of head member (reference character 12) and are not circulating fluid near the lower surface of module 13 are not particularly efficient in removing heat generated by the module. Increasing the flow of fluid through the conduits near module 13 would more effectively cool the module. Second, fluid apparently flows through the heat sink both when tip 14 is being cooled and when the direction of current flowing through module 13 is reversed so that the lower surface of the module 13 to produce cold and the upper surface to produce heat for tip 14. Operation of the cooling heat sink during heating of tip 14 draws more heat away from the upper surface of module than if fluid were not flowing through the heat sink and thus increases the electrical consumption of the probe.

Both Yardley and Eidus disclose pulp testers which continuously run current through the thermoelectric module when the apparatus is being used. Ordinarily, the metallic probe of the pulp tester will, after reaching a selected temperature, maintain an appropriately high temperature for a period of time after the flow of current through the module is discontinued; hence, maintaining a continuous flow of current through the module is not necessary, especially if the removal of heat by the cooling heat sink is prevented or minimized.

Accordingly, it would be highly desirable to provide an improved thermoelectric dental pulp tester of the type described which minimized the electricity consumed during operation of the pulp tester and minimized the temperature reached by the metal probe thereof when the probe was being heated by current flowing through the thermoelectric module in the pulp tester.

It would also be highly desirable to provide an improved thermoelectric dental pulp tester including a fluid cooled heat sink which would draw away heat produced by the thermoelectric module during cooling of the probe but which would not cool the thermoelectric module during heating of the dental probe.

Therefore, it is a principal object of the present invention to provide an improved thermoelectric dental pulp tester.

A further and more specific object of the invention is to provide an improved thermoelectric dental pulp tester including a thermally conductive probe which is contacted with a tooth to determine if the tooth is alive and including a thermoelectric module for generating heat and cold which are separately and alternately conducted through the probe to the tooth surface, the thermoelectric module comprising a group of semiconductor elements connected at their ends by a pair of opposed groups of electrically conductive plates to form an electrical series of the semiconductor elements, each of the pair of groups of plates constituting hot junctions when electrical current passes through the series in one direction and constituting cold junctions when electrical current passes through the series of elements in the reverse direction.

A further object of the invention is to provide an improved thermoelectric dental pulp tester of the type described which minimizes the amount of electricity consumed during operation of the probe and extends the operational life of the semiconductor elements comprising the thermoelectric module.

Another object of the invention is to provide an improved thermoelectric tooth pulp tester having a fluid cooled heat sink which draws away heat produced by the thermoelectric module during cooling of the probe but which does not cool the module during the heating of the dental probe.

Yet another object of the invention is to provide an improved thermoelectric dental pulp tester which, in order to minimize the electrical consumption of the tester, only permits the thermoelectric module to generate electricity for intermittent relatively short periods of time and notifies the user when the probe is heated or cooled and ready to be applied to a patient's tooth.

These and other, further and more specific objects and advantages of the invention will be apparent to those skilled in the art from the following detailed description thereof, taken in conjunction with the drawings, in which:

FIG. 1 is a perspective view of a dental pulp tester constructed in accordance with the invention;

FIG. 2 is a sectional view of the hand held dental probe unit of FIG. 1 taken along section line 2—2 thereof and further illustrating the interior construction thereof;

FIG. 3 is a partial section view of the probe unit of FIG. 2 taken from within the area circumscribed by dashed circle 3 thereof;

FIG. 4 is a partial top sectional view of the probe unit of FIG. 2 taken along section line 4—4 thereof;

Figure 5:
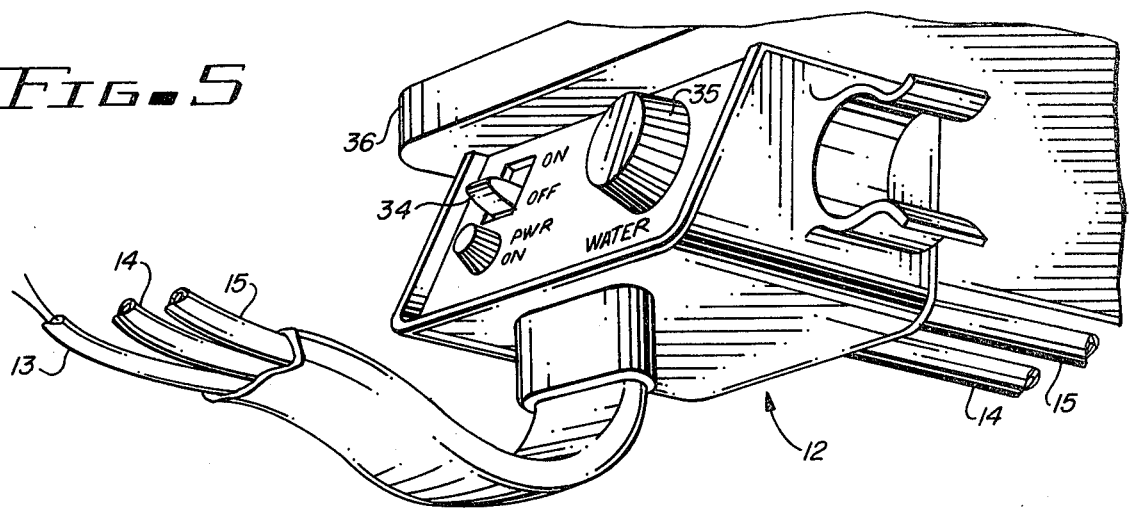
FIG. 5 is a perspective view of an optional control unit for the dental probe unit of FIG. 2.

Briefly, in accordance with my invention, I provide apparatus for applying heat and cold to a tooth to determine if the nerves in the pulp of the tooth are alive. The apparatus includes a housing; a thermoelectric module carried in the housing and including a plurality of semiconductor elements connected at their ends by a pair of opposed groups of electrically conductive plates to form an electrical series of the semiconductor elements, each of the pair of groups constituting hot junctions when electrical current passes through said series in one direction and constituting cold junctions when electrical current passes through said series in the reverse direction; a primary heat transfer member in thermally conductive contact with one of the pair of plate groups; a secondary heat transfer member in thermally conductive contact with the other of the pair of groups of plates, the secondary heat transfer member including a thermally conductive casing and passage means formed within the casing to receive and carry fluid therethrough and including at least one inlet and one outlet opening, the fluid absorbing and transporting heat away from the casing; an intake conduit for directing fluid into the inlet opening of the passage means; a discharge conduit for receiving fluid flowing through the outlet opening of the passage means; a pump for imparting motive power to and directing the fluid through the conduits and the passage means; terminals for making electrical contact to the thermoelectric module; a source of current electrically connected to the terminals; normally closed switch means connected between the terminals and the current source; an elongate probe member of heat conductive material in thermally conductive contact with the primary heat transfer member; and, a thermocouple unit in thermally conductive contact with said primary heat transfer member for measuring the temperature of said primary heat transfer member and for causing the switch means to open when the temperature of the primary heat transfer member reaches a preselected level.

The dental pulp testing apparatus may also include a mechanism for preventing the flow of fluid through the passage means of the secondary heat transfer member when the probe member is being heated.

Turning now to the drawings, which depict the presently preferred embodiments of the invention for the purpose of illustrating the practice thereof and not by way of limitation of the scope of the invention and in which like reference characters represent corresponding elements throughout the several views, FIGS. 1 to 4 illustrate the presently preferred embodiment of the invention including a probe unit and control unit respectively indicated by reference characters 11 and 12 and interconnected by electrical lines 13. Conduits 14 and 15 deliver and carry away water 19 or other fluid to and from heat sink 31 having passageway 16 and inlet 17 and outlet 18 formed in the thermally conductive member 10 comprising the heat sink 31. Heat sink 31 is positioned below and in thermally conductive contact with thermoelectric module 20. Electric line 13 are received by terminals 23 of module 20. Metal probe 21 is in thermally conductive contact with heat 22. Heat sink 22 is preferably composed of a silver-copper alloy and is in thermally conductive contact with electrical plates which interconnect upper portions of semiconductor elements composing thermoelectric module 20. Electrical plates which interconnect lower portions of the semiconductor elements of module 20 are in thermal contact with heat sink 31. When current is passed through electrical lines 13 and module 20 in one direction the upper electrical plates of module 20 are hot and the lower plates cold. When the direction of current flowing through the module 20 is reversed the upper plates generate cold while the lower plates become hot. Switch 24 controls the direction of current through module 20. If switch 24 is in the "H" position, probe 21 is heated and switch 24 automatically stops the flow of water or other fluid through heat sink 19 by turning off the pump (not shown) which directs fluid through conduits 14, 15 and passageway 16 or by closing a valve positioned along conduits 14, 15 or passageway 16. When the temperature of heat sink 22 rises to a preselected level, thermocouple unit 25 activates normally closed switch 33 (not shown) positioned along electrical lines 13 or positioned in control unit 12 to stop the flow of current through lines 13 connected to module 20. As soon as the flow of electricity through lines 13 is stopped, light 26 is activated to signal the user that the probe 21 is heated and ready to use. After the temperature of heat sink 22 falls below a selected level, thermocouple 25 closes switch 33 to allow module 20 to again generate heat for probe 21. When current if flowing through module 20, light 26 is off. Moving switch 24 to the "C" position allows water to flow through heat sink 16 to dissipate heat which rapidly generates in the electrical plates along the bottom surfaces of the semiconductors comprising module 20. After the temperature of heat sink 22 is cooled to a preselected level by module 20, thermocouple 25 opens switch 33 and light 27 is activated to signal the user that probe 21 is cooled and ready for use. Water continuously flows through heat sink 31 when switch 24 is in the "C" position. The housing 30 of probe member 11 includes insulating material 28 and a covering of hard, chemical resistant material 29.

The control unit 12 seen in FIG. 1 includes switch 34 for turning on the power which flows through lines 13 and thermoelectric module 20 to generate heat and cold. As earlier described, thermocouple unit 25 intermittently stops the flow of current through lines 13 by opening a switch when probe 21 is heated or cooled to a particular temperature. In this regard, thermocouple 25 may control switch 34 or an auxiliary switch 33 located in control unit 12 or along lines 13. Knob 35 adjusts the rate of flow of fluid 19 through conduits 14, 15.

Figure 6:
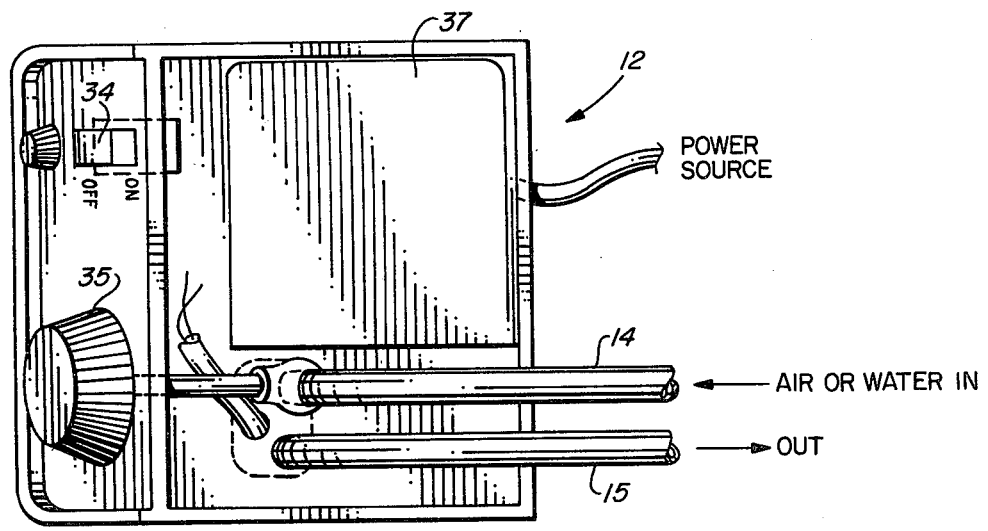
FIG. 6 is a top view of the control unit of FIG. 5 illustrating the interior construction thereof.

An alternate configuration for control unit 12 is illustrated in FIGS. 5, 6 where unit 12 is adapted to be mounted on dental tool tray 36 and includes a rechargeable battery power source 37. Power source 37 may, of course, comprise members which merely transport electricity to probe unit 11 when an extension cord leading to control unit 12 is plugged into an electrical wall socket.

The improved probe of the invention markedly increases the operational life of the semiconductor elements comprising photoelectric module 20 and decreases electrical consumption of the probe by automatically limiting the maximum temperature to which probe 21 can be heated and by stopping the flow of current to photoelectric module 20 if the temperature of heat sink 22 falls within a predetermined range when probe 21 is heated or cooled. Cutting off the flow of fluid through cooling heat sink 31 when switch 24 is in the "H" or heating position also decreases the amount of electricity required to heat probe 21.

Having described my invention in such terms as to enable those skilled in the art to understand and practice it, and having identified the presently preferred embodiments thereof, I claim:

1. Apparatus for applying heat and cold to a tooth to determine if the nerves in the pulp of the tooth are alive, comprising,
   (a) a housing;
   (b) a thermoelectric module carried in said housing including a plurality of semiconductor elements connected at their ends by a pair of opposed groups of electrically conductive plates to form an electrical series of said semiconductor elements, each of said pair of plate groups constituting hot junctions when electrical current passes through said series in one direction and constituting cold junctions when electrical current passes through said series in the reverse direction,
   (c) a primary heat transfer member in thermally conductive contact with one of said pair of plate groups,
   (d) a secondary heat transfer member in thermally conductive contact with the other of said pair of groups of plates, said secondary heat transfer member including
      (i) a thermally conductive casing, and
      (ii) passage means formed within said casing to receive and carry fluid therethrough and including at least one inlet and one outlet opening, said fluid absorbing and transporting heat away from said casing,
   (e) an intake conduit for directing fluid into said inlet opening of said passage means,
   (f) a discharge conduit for receiving fluid flowing through said outlet opening,
   (g) a pump for imparting motive power to and directing said fluid through said conduits and said passage means,
   (h) terminals for making electrical contact with said thermoelectric module,
   (i) a source of current electrically connected to said terminals,
   (j) normally closed switch means connected between said terminals and said current source,
   (k) an elongate probe member of heat conductive material in thermally conductive contact with said primary heat transfer member; and,
   (l) a thermocouple unit in thermal contact with said primary heat transfer member for measuring the temperature of said primary heat transfer member and for causing said switch means to open when the temperature of said primary heat transfer member reaches a preselected level.

2. The apparatus of claim 1 including electrically activated means for preventing the flow of fluid through said passage means.

3. The apparatus of claim 2 wherein said thermocouple activates said fluid flow prevention means to stop the flow of fluid through said passage means when the temperature of said primary heat transfer member reaches said preselected level.

* * * * *